United States Patent [19]

Reichenbacher et al.

[11] 3,998,851

[45] Dec. 21, 1976

[54] PREPARATION OF COUMARINS

[75] Inventors: Paul H. Reichenbacher, Schaumburg; Theresa M. Forsythe, Mount Prospect; Allen K. Sparks, Woodstock, all of Ill.

[73] Assignee: Universal Oil Products Company, Des Plaines, Ill.

[22] Filed: June 30, 1975

[21] Appl. No.: 591,994

Related U.S. Application Data

[63] Continuation-in-part of Ser. No. 358,197, May 7, 1973, abandoned.

[52] U.S. Cl. ........................................ 260/343.2 R
[51] Int. Cl.$^2$ ...................................... C07D 311/10
[58] Field of Search ............................ 260/343.2 R

[56] References Cited

UNITED STATES PATENTS

| 3,259,635 | 7/1966 | Ritter et al. | 260/343.2 |
| 3,322,794 | 5/1967 | Haeberli | 260/343.2 |
| 3,803,175 | 4/1974 | Sparks et al. | 260/343.2 |

*Primary Examiner*—John M. Ford
*Attorney, Agent, or Firm*—James R. Hoatson, Jr.; Raymond H. Nelson; William H. Page, II

[57] ABSTRACT

Coumarin compounds may be produced by the conversion of o-hydroxycinnamates or o-hydroxycinnamic acids in the presence of catalysts comprising compounds containing metals of Group VIII of the Periodic Table.

11 Claims, No Drawings

PREPARATION OF COUMARINS

CROSS REFERENCE TO RELATED APPLICATIONS

This application is a continuation-in-part of our copending application Ser. No. 358,197 filed May 7, 1973, now abandoned, all teachings of which are incorporated herein by reference thereto.

BACKGROUND OF THE INVENTION

The prior art has shown that compounds such as methyl o-hydroxycinnamate may be converted to coumarin by utilizing a thermal process in which the o-hydroxycinnamate may be heated to a temperature above 200° C. for a relatively long period of time to convert the aforesaid methyl o-hydroxycinnamate to coumarin. However, when the products which were obtained from a phenol-methyl acrylate reaction and which comprise coumarin as well as methyl o-hydroxycinnamate were maintained at a temperature of 90° C. in the absence of oxygen but without the addition of any catalyst, there was not a further conversion of the methyl o-hydroxycinnamate to coumarin. In contradistinction to this, when methyl o-hydroxycinnamate was treated with a catalyst of the type hereinafter set forth in greater detail at a temperature of 90° C., there was a substantial conversion of the methyl o-hydroxycinnamate to coumarin with a substantial selectivity. Other prior art patents have shown that compounds such as m-aminophenol may be condensed with various acrylic acids in a Lewis acid-catalyzed reaction to form 7-aminocoumarins following oxidation by nitrobenzene compounds. However, as will hereinafter be shown in greater detail, it has now been discovered that by utilizing a catalyst which contains a metal of Group VIII of the Periodic Table, either in solid or soluble form, it is possible to convert o-hydroxycinnamates or o-hydroxycinnamic acids to coumarin compounds without having to use the strong acid catalysts such as the Lewis acids which have been utilized in the past. Likewise, the unexpected discovery that these compounds containing a metal of Group VIII of the Periodic Table can be used as catalysts to effect the conversion of the aforesaid compounds to coumarin compounds takes the present invention outside of the scope of the classical Perkin condensation reaction which also is effected in the presence of acid catalysts.

This invention relates to a process for the conversion of ortho-coumaric acids or ortho-coumarates to coumarins. More specifically, the invention relates to a process for converting these compounds which, in the present specification and appended claims, are also referred to as o-hydroxycinnamic acids and o-hydroxycinnamates to coumarins in the presence of certain catalytic compositions of matter, said catalyst containing a metal of Group VIII of the Periodic Table.

Coumarins which are organic compounds, some of which possess fragrant odors, may be used as deodorizing and odor-enhancing agents in cosmetics and toiletry articles such as perfumes, colognes, soaps, talcs, bath powders, or in other products such as tobacco, inks, rubbers, etc., where aromatic ingredients are required. Certain coumarin compounds, especially certain hydroxycoumarins, are fluorescent organic compounds which may be used as whiteners for cloth in laundry soaps, as sun-screen agents in skin care formulations, and as dyes useful in modulating electromagnetic energy outputs from laser equipment. These compounds may be prepared by trans-cis isomerization and lactonizaton reactions in which o-hydroxycinnamates or o-hydroxycinnamic acids of the type hereinafter set forth in greater detail are cyclized in the presence of certain catalytic compositions of matter.

It is therefore an object of this invention to provide a process for the conversion of certain o-hydroxycinnamates and o-hydroxycinnamic acids to coumarins.

In one aspect an embodiment of this invention resides in a process for the preparation of a coumarin which comprises contacting a reactive compound consisting essentially of an o-hydroxycinnamate, an o-hydroxycinnamic acid or a mixture thereof with a solid or liquid catalyst containing a metal of Group VIII of the Periodic Table at a temperature in the range of from about 25° to about 200° C. and a pressure in the range of from about atmospheric to about 100 atmospheres, and recovering the resultant coumarin.

A specific embodiment of this invention is found in a process for the preparation of a coumarin which comprises contacting methyl o-hydroxycinnamate with a catalyst comprising palladium composited on a carbon support at a temperature in the range of from about 25° to about 200° C. and a pressure in the range of from about atmospheric to about 100 atmospheres, and recovering the resultant coumarin.

Other objects and embodiments will be found in the following further detailed description of the present invention.

As hereinbefore set forth the present invention is concerned with a process for converting ortho-coumarates (o-hydroxycinnamates) or ortho-coumaric acids (o-hydroxycinnamic acids) to coumarin compounds which are important industrial chemicals. Conversions of the starting materials are effected by treating said materials at conversion conditions in the presence of a catalyst comprising a compound containing a metal of Group VIII of the Periodic Table. The conversion conditions which are employed to effect the reactions of the present invention will include temperatures in the range of from about 25° up to about 200° C. and preferably in a range of from about 25° (ambient) to about 180° C. While in the preferred embodiment of the invention the conversion reactions are effected at pressures ranging from atmospheric up to about 20 atmospheres, it is also contemplated that superatmospheric pressures ranging up to about 100 atmospheres or more may be employed. When utilizing superatmospheric pressures, the pressures are afforded by the introduction of a substantially inert gas such as nitrogen into the reaction zone, the particular amount of pressure which is used being that which is necessary to maintain a major portion of the reactants in the liquid phase.

Examples of o-hydroxycinnamates (ortho-coumarates) or o-hydroxycinnamic acids (ortho-coumaric acids) which may be converted to coumarins according to the process of this invention will include those compounds having the formula:

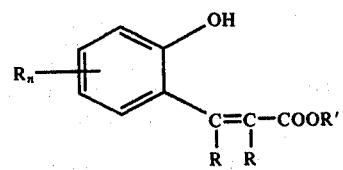

in which n ranges from 0 to 4, R is selected from the group consisting of hydrogen, alkyl, cycloalkyl, aryl, alkaryl, aralkyl, hydroxyl, alkyloxy, cycloalkyloxy, aryloxy, alkaryloxy, aralkyloxy, carboxyl, cyano, fluoro, chloro, bromo, iodo, amino, alkylamino, cycloalkylamino, arylamino, alkarylamino, aralkylamino, nitro, nitroso, amide, formyl, acetyl, propionyl, butyroyl, benzoyl, and vinyl radicals and R' is selected from the group consisting of hydrogen, alkyl, cycloalkyl, aryl, alkaryl and aralkyl radicals. Some specific examples of these compounds will include o-hydroxycinnamic acid, alkyl coumarates in which the alkyl group, R', will contain from 1 to about 4 carbon atoms such as methyl o-hydroxycinnamate, ethyl o-hydroxycinnamate, n-propyl o-hydroxycinnamate, isopropyl o-hydroxycinnamate, n-butyl o-hydroxycinnamate, t-butyl o-hydroxycinnamate, n-amyl o-hydroxycinnamate, etc.; aryl o-hydroxycinnamates such as phenyl o-hydroxycinnamate, naphthyl o-hydroxycinnamate, anthracyl o-hydroxycinnamate, etc.; cycloalkyl o-hydroxycinnamates such as cyclopentyl o-hydroxycinnamate, cyclohexyl o-hydroxycinnamate, methylcyclopentyl o-hydroxycinnamate, cycloheptyl o-hydroxycinnamate, etc.; alkaryl o-hydroxycinnamates such as o-tolyl o-hydroxycinnamate, m-tolyl o-hydroxycinnamate, p-tolyl o-hydroxycinnamate, o-ethylphenyl o-hydroxycinnamate, m-ethylphenyl o-hydroxycinnamate, p-ethylphenyl o-hydroxycinnamate, etc.; aralkyl o-hydroxycinnamates such as benzyl o-hydroxycinnamate, o-methylbenzyl o-hydroxycinnamate, m-methylbenzyl o-hydroxycinnamate, p-methylbenzyl o-hydroxycinnamate, etc.; ring-substituted o-hydroxycinnamic acids and ring-substituted o-hydroxycinnamates such as 3-(2'-hydroxy-3'-methylphenyl)acrylic acid, 3-(2'-hydroxy-4'-methylphenyl)-acrylic acid, 3-(2'-hydroxy-5'-methylphenyl)-acrylic acid, 3-(2'-hydroxy-6'-methylphenyl)-acrylic acid, 3-(2'-hydroxy-3',4'-dimethylphenyl)-acrylic acid, methyl 3-(2'-hydroxy-3',5'-dimethylphenyl)-acrylate, ethyl 3-(2'-hydroxy-3',6'-dimethylphenyl)-acrylate, n-propyl 3-(2'-hydroxy-4',5'-diethylphenyl)-acrylate, t-butyl 3-(2'-hydroxy-4',5',6'-trimethoxyphenyl)-acrylate, cyclohexyl 3-(2'-hydroxy-3',4',5',6'-tetramethylphenyl)-acrylate, methyl 3-(2',3'-dihydroxyphenyl)-acrylate, methyl 3-(2',5'dihydroxyphenyl)acrylate, ethyl 3-(2',4',6'-trihydroxyphenyl)-acrylate, isopropyl 3-(2'-hydroxy-5'-phenylphenyl)-acrylate, phenyl 3-(2'-hydroxy-4'-carbomethoxyphenyl)-acrylate, naphthyl 3-(2'-hydroxy-6'-cyanophenyl)-acrylate, methyl 3-(2'-hydroxy-4',5'-methylenedioxyphenyl)-acrylate, methyl 3-(2'-hydroxy-5'-aminophenyl)-acrylate, sec-butyl 3-(2'-hydroxy-4'-chlorophenyl)-acrylate, etc.; vinyl-substituted o-hydroxycinnamic acids and o-hydroxycinnamates such as 2-methyl-3-(2'-hydroxyphenyl)-acrylic acid, 3-methyl-3-(2'-hydroxyphenyl)-acrylic acid, 2,3-dimethyl-3-(2'-hydroxyphenyl)-acrylic acid, 2-ethyl-3-(2'-hydroxyphenyl)-acrylic acid, 2-methyl-3-(2',5'-dihydroxyphenyl)-acrylic acid, methyl 2-methyl-3-(2'-hydroxyphenyl)acrylate, ethyl 2-phenyl-3-(2'-hydroxy-5'-methylphenyl)-acrylate, n-propyl 2-benzyl-3-(2'-hydroxyphenyl)-acrylate, methyl 2-p-tolyl-3-(2'-hydroxyphenyl)-acrylate, etc. It is to be understood that these compounds are only representative of the class of o-hydroxycinnamates and o-hydroxycinnamic acids which may be converted to coumarins and that the present invention is not necessarily limited thereto.

The catalytic compositions of matter which are to be employed to effect the process of the present invention will comprise a compound containing a metal of Group VIII of the Periodic Table. In the preferred embodiment of the invention that catalyst will be in solid form, some specific examples of these catalysts being platinum composited on a solid support such as platinum composited on alumina, platinum composited on silica, platinum composited on a carbon support such as charcoal, platinum composited on a diatomaceous earth, platinum composited on an aluminosilicate such as faujasite, mordenite, etc., platinum metal, palladium composited on alumina, palladium composited on silica, palladium composited on charcoal, palladium composited on a diatomaceous earth, palladium composited on an aluminosilicate, palladium powder, the corresponding nickel, cobalt, iron, ruthenium, rhodium, osmium and iridium metals composited on alumina, silica, carbon, diatomaceous earth, aluminosilicates, etc. While as hereinbefore set forth, in the preferred embodiment of the invention, the catalyst is in solid form, it is also contemplated within the scope of this invention that soluble salts containing a metal of Group VIII of the Periodic Table may also be used, although not necessarily with equivalent results. Some specific examples of these soluble Group VIII metal salts which may be used will include platinum chloride, platinum nitrate, platinum acetate, platinum acetylacetonate, palladium chloride, palladium nitrate, palladium acetate, palladium acetylacetonate, nickel chloride, nickel nitrate, nickel acetate, nickel acetylacetonate, cobalt chloride, cobalt nitrate, cobalt acetate, cobalt acetylacetonate, etc. It is to be understood that the aforementioned catalysts, both solid and soluble in nature, are only representative of the class of compounds which may be employed to effect the reaction, and that the present invention is not necessarily limited thereto.

The process of the present invention involving the conversion of a compound of the type hereinbefore set forth in greater detail to a coumarin or coumarins may be effectd in any suitable manner and may comprise either a batch or continuous type of operation. For example, when a batch type operation is used, a quantity of the compound which is to undergo conversion is placed in an appropriate apparatus. In the event that the reaction is to be effected at atmospheric pressure this apparatus may comprise a flask equipped with appropriate stirring and reflux equipment. Alternatively, if the reaction is to be effected under superatmospheric conditions the apparatus will comprise a pressure-resistant piece of equipment such as an autoclave of the rotating or mixing type. If so desired, a substantially inert organic solvent such as n-pentane, n-hexane, n-heptane, cyclopentane, cyclohexane, cycloheptane, methylcyclopentane, benzene, toluene, the xylenes, phenol, acetic acid, propionic acid, etc., may also be present in the reaction zone. The reaction apparatus is then pressured to the desired operating pressure by means of a substantially inert gas such as nitrogen, if superatmospheric pressures are to be employed, and heated to the desired operating temperature in the range hereinbefore set forth. After maintaining the apparatus and contents thereof at this temperature for a predetermined period of time which may range from about 0.5 up to about 16 hours or more in duration, heating is discontinued. The apparatus and contents thereof are allowed to return to room temperature, any excess pressure if present is vented and the reaction mixture is recovered therefrom. The reaction mixture is then subjected to conventional means of separation and purification including filtration, washing, drying, extraction, fractional distillation, etc., whereby the desired product comprising a coumarin or coumarins is separated and recovered.

It is also contemplated within the scope of this invention that the process for converting a compound of the type hereinbefore set forth to a coumarin or coumarins may be effected in a continuous manner of operation. When such a type of operation is employed, the starting material comprising the compound is continuously charged to a reaction vessel containing the particular catalyst and which is maintained at the proper operating conditions of temperature and pressure. After being maintained in the apparatus for a predetermined period of time, the reactor effluent is continuously withdrawn and subjected to separation steps similar in nature to those hereinbefore set forth whereby the desired coumarin(s) is (are) separated and recovered while any unreacted starting materials are recycled to the reaction zone to form a portion of the feed stock. Inasmuch as the catalyst, in the preferred form, is solid in nature the continuous method of operation may be effected in several ways. One type of operation which may be employed constitutes a fixed bed method in which the catalyst is disposed in the reactor as a fixed bed and the starting materials are passed through said bed in either an upward or downward flow. Another type of operation which may be used constitutes the moving bed type of operation in which the catalyst and the reactant are passed through the reaction zone either concurrently or countercurrently to each other. Yet another type of operation which may be used is the slurry type of operation in which the catalyst is carried into the reaction zone as a slurry in the reactant. In each type of operation the reactor effluent is continuously withdrawn and treated in a manner similar to that hereinbefore set forth whereby the desired product is recovered and the reactant starting material is recycled to the reaction zone to form a portion of the feed stock therein.

The following examples are given to illustrate the process of the present invention. However, these examples are not intended to limit the generally broad scope of the present invention in strict accordance therewith.

EXAMPLE I

In this example, methyl o-hydroxycinnamate and coumarin were prepared by reacting 3.00 moles of phenol, 1.21 moles of methyl acrylate, 0.024 mole of cupric acetate monohydrate, 0.012 mole of palladium acetate, 65 grams of propionic acid, 65 grams of cyclohexane, and 6 grams of a diatomaceous earth known in the trade as Celite Hyflo Super-Cel at 90° C. for 6 hours in a 1 liter, stirred, stainless steel autoclave as air was bubbled through the liquid contents at 1 ft$^3$/hr (corrected to standard temperature and pressure), the contents of the autoclave being maintained at a pressure of 250 psig during this period of time. At the end of this period, analysis of the liquid contents by gas-liquid chromatography demonstrated the presence of 0.18 mole of methyl o-hydroxycinnamate and 0.14 mole of coumarin plus other products, unreacted reactants, and solvents.

To demonstrate that methyl o-hydroxycinnamate is not readily converted to coumarin by heating at 90° C. in the absence of an added catalyst containing a Group VIII metal, the gaseous contents of the autoclave were vented from 250 psig to 50 psig and then repressured to 250 psig with nitrogen. After one hour of simultaneously maintaining the autoclave contents at 90° C., purging these liquid contents with nitrogen at 1 ft$^3$/hr (corrected to standard temperature and pressure), and maintaining the autoclave contents at 250 psig, analysis of the liquid contents by gas-liquid chromatography again revealed the presence of 0.18 mole of methyl o-hydroxycinnamate and 0.14 mole of coumarin, thus affirming the fact that there was no additional conversion of methyl o-hydroxycinnamate to coumarin.

EXAMPLE II

In this example methyl o-hydroxycinnamate was prepared by refluxing a solution comprising 400 cc of methanol, 50 grams of o-hydroxycinnamic acid and 2 grams of p-toluenesulfonic acid for a period of 8 hours followed by removal of about 200 cc of the methanol on a steam bath. Following this 500 cc of water was added and the resulting solution extracted with ether. The ether extracts were washed with a sodium carbonate solution and then with water. This was followed by drying the ether extracts over anhydrous sodium sulfate and evaporation of the ether to produce solid methyl o-hydroxycinnamate. The solid was recrystallized from methanol and from benzene to produce the desired crystalline o-hydroxycinnamate.

To illustrate the fact that methyl o-hydroxycinnamate can be converted to coumarin by treatment in the presence of a catalyst containing a metal of Group VIII, 50 mmoles of the methyl o-hydroxycinnamate prepared according to the above paragraph and 0.5 mmoles of a catalyst comprising 5% palladium composited on charcoal along with 60 grams of acetic acid were placed in a stirred glass reactor which was heated by an oil bath to a temperature of 90° C. The reaction was effected under a stream of nitrogen at atmospheric pressure. At the end of 10 hours there was a 93% selectivity to coumarin obtained based on the converted methyl o-hydroxycinnamate.

EXAMPLE III

To illustrate the use of a mixed solvent system another experiment was run in which 22 mmoles of methyl o-hydroxycinnamate and 0.5 mmoles of a catalyst comprising a 5% palladium composited on charcoal were placed in a stirred glass reactor. In addition, 5.2 grams of acetic acid and 47 grams of phenol were placed in the reactor which was then heated to a temperature of 110° C. under an atmosphere of nitrogen. At the end of 2 hours there was a 90% selectivity to coumarin with 7% of the methyl o-hydroxycinnamate remaining, at the end of 3 hours a 100% selectivity to coumarin with 7% of the methyl o-hydroxycinnamate remaining, and at the end of 5.5 hours an 89% selectivity to coumarin with 5% of the methyl o-hydroxycinnamate remaining.

EXAMPLE IV

To illustrate the use of a different solid catalyst, 22 mmoles of methyl o-hydroxycinnamate along with 0.8 mmoles of a catalyst comprising 8.3% palladium composited on a diatomaceous earth were placed in a stirred glass reactor along with 5 grams of acetic acid and 47 grams of phenol. The reactor was heated by means of an oil bath to a temperature of 110° C. under a nitrogen atmosphere. At the end of 1 hour there was a 17% selectivity to coumarin with 73% of the methyl o-hydroxycinnamate remaining, at the end of 2 hours a 64% selectivity to coumarin with 50% of the methyl o-hydroxycinnamate, at the end of 3 hours a 76% selectivity to coumarin with 5% of the methyl o-hydroxycinnamate remaining, at the end of 4 hours the percent of selectivity was raised to 95%, and at the end of 5.5 hours there was a 100% selectivity to coumarin with no methyl o-hydroxycinnamate remaining.

EXAMPLE V

In this example 14 mmoles of methyl o-hydroxycinnamate and 1.7 mmoles of a catalyst comprising 20% nickel composited on charcoal were treated in a manner similar to that set foth in the above examples by heating the mixture in 60 grams of acetic acid to a temperature of 100° C., in a nitrogen atmosphere. The percent selectivity to coumarin was 100% at the end of 1.5 hours, 75% at the end of 4.5 hours, and 33% at the end of 5.5 hours.

EXAMPLE VI

As an illustration of the use of a soluble catalyst containing a metal of Group VIII of the Periodic Table, 10 mmoles of methyl o-hydroxycinnamate and 0.3 mmoles of palladium (II) acetylacetonate in 50 grams of acetic acid were heated to a temperature of 110° C. in a stirred glass reactor, said heat being supplied by means of an oil bath. In this experiment the conversion was run in an atmosphere of air. At the end of 1.5 hours there was a 50% selectivity to coumarin obtained, and at the end of 4 hours a 57% selectivity to coumarin was obtained.

EXAMPLE VII

To a stirred glass reactor is added 10 mmoles of coumaric acid, 0.5 mmoles of platinum composited on a gamma-alumina support and 60 grams of acetic acid. The reactor is heated to a temperature of 100° C. by means of an oil bath while effecting the reaction in a nitrogen atmosphere. At the end of 4 hours, it will be found that a major portion of the cinnamic acid is cyclized to form coumarin.

EXAMPLE VIII

In like manner a solution cnsisting of 10 mmoles of phenyl o-hydroxycinnamate, 0.5 mmoles of a catalyst comprising palladium composited on charcoal, 5 grams of acetic acid and 50 grams of phenol is heated to a temperature of 110° C. under a blanket of nitrogen. At the end of 5 hours, it will be found that a major portion of phenyl o-hydroxycinnamate is converted to coumarin.

EXAMPLE IX

In this example 20 mmoles of cyclohexyl o-hydroxycinnamate and 0.5 mmoles of a catalyst comprising palladium composited on a diatomaceous earth, known in the trade as Celite, along with 5 grams of acetic acid and 50 grams of phenol are heated to a temperature of 100° C. under a blanket of nitrogen. At the end of 4 hours, it will be found that coumarin is obtained from the reaction.

EXAMPLE X

In this example 10 mmoles of p-tolyl o-hydroxycinnamate and 0.5 mmoles of platinum composited on a diatomaceous earth along with 60 grams of acetic acid are heated to a temperature of 110° C. under a blanket of nitrogen, said reaction being effected in a stirred glass reactor which is heated by means of an oil bath. At the end of a 5 hour residence time it will be determined by means of a gas-liquid chromatographic analysis that coumarin was formed during the reaction.

EXAMPLE XI

In this example 20 mmoles of methyl 3-(2',5'-dihydroxyphenyl)acrylate, 0.5 mmoles of rhodium composited on a diatomaceous earth, and 70 grams of propionic acid are heated to 180° C. under 20 atmospheres of nitrogen in a stirred, stainless steel autoclave. At the end of 1 hour the autoclave and its contents are allowed to cool to room temperature, the excess pressure is vented, and the product is recovered. A major portion of the organic product will be 6-hydroxycoumarin.

EXAMPLE XII

In this example a solution comprised of 30 mmoles of 2-methyl-3-(2'-hydroxyphenyl)-acrylic acid and 100 grams of propionic acid are percolated downwards through a glass cylinder containing a fixed bed of a catalyst consisting of 5% ruthenium on mordenite at 120° C. The organic effluent will be found to contain a substantial amount of 3-methylcoumarin.

We claim as our invention:

1. A process for the preparation of a coumarin which comprises contacting a reactant consisting essentially of an o-hydroxycinnamate, an o-hydroxycinnamic acid or a mixture thereof with a solid or dissolved catalyst containing a metal of Group VIII of the Periodic Table at a temperature in the range of from about 25° to about 200° C. and a pressure in the range of from about atmospheric to about 100 atmospheres, and recovering the resultant coumarin.

2. The process as set forth in claim 1 in which said catalyst is palladium on a carbon support.

3. The process as set forth in claim 1 in which said catalyst is palladium on a diatomaceous earth support.

4. The process as set forth in claim 1 in which said catalyst is platinum on an alumina support.

5. The process as set forth in claim 1 in which said catalyst is palladium powder.

6. The process as set forth in claim 1 in which said catalyst is palladium (II) acetylacetonate.

7. The process as set forth in claim 1 in which said reactant which is converted to a coumarin is methyl o-hydroxycinnamate.

8. The process as set forth in claim 1 in which said reactant which is converted to a coumarin is o-hydroxycinnamic acid.

9. The process as set forth in claim 1 in which said reactant which is converted to a coumarin is phenyl o-hydroxycinnamate.

10. The process as set forth in claim 1 in which said reactant which is converted to a coumarin is methyl 3-(2',5'-dihydroxyphenyl)-acrylate.

11. The process as set forth in claim 1 in which said reactant which is converted to a coumarin is methyl 2methyl-3-(2'-hydroxyphenyl)-acrylate.

* * * * *